United States Patent
Marciano et al.

(10) Patent No.: US 10,329,609 B2
(45) Date of Patent: Jun. 25, 2019

(54) UNIVERSAL DNA PROFILING

(71) Applicants: Michael Marciano, Manlius, NY (US); Molly Cadle-Davidson, Geneva, NY (US)

(72) Inventors: Michael Marciano, Manlius, NY (US); Molly Cadle-Davidson, Geneva, NY (US)

(73) Assignee: Syracuse University, Syracuse, NY (US)

( * ) Notice: Subject to any disclaimer, the term of this patent is extended or adjusted under 35 U.S.C. 154(b) by 253 days.

(21) Appl. No.: 15/274,439

(22) Filed: Sep. 23, 2016

(65) Prior Publication Data

US 2017/0088889 A1    Mar. 30, 2017

Related U.S. Application Data

(60) Provisional application No. 62/232,007, filed on Sep. 24, 2015.

(51) Int. Cl.
| | |
|---|---|
| *C12Q 1/68* | (2018.01) |
| *G06F 19/18* | (2011.01) |
| *C12Q 1/6869* | (2018.01) |
| *G16B 20/00* | (2019.01) |
| *C12Q 1/6888* | (2018.01) |
| *C12Q 1/6895* | (2018.01) |
| *G16B 50/00* | (2019.01) |

(52) U.S. Cl.
CPC ............ *C12Q 1/6869* (2013.01); *G16B 20/00* (2019.02); *C12Q 1/6888* (2013.01); *C12Q 1/6895* (2013.01); *G16B 50/00* (2019.02)

(58) Field of Classification Search
CPC .......................... C12Q 1/6869; C12Q 1/6888
See application file for complete search history.

(56) References Cited

U.S. PATENT DOCUMENTS

| | | | |
|---|---|---|---|
| 2012/0129794 A1 | 5/2012 | Dowd et al. | |
| 2017/0138845 A1* | 5/2017 | Birarda | G01N 21/35 |

OTHER PUBLICATIONS

International Search Report and Written Opinion Form PCT/ISA/220, International Application No. PCT/US16/54617, p. 1-9, dated Dec. 20, 2016.
Thomsen et al. Detection of a Diverse Marine Fish Fauna Using Environmental DNA from Seawater Samples PLOS One, Aug. 2012, vol. 7, Issue 8, pp. 1-9.
Pereira, et al. "Identification of Species with DNA-Based Technology: Current Progress and Challenges" Recent Patents on DNA & Gene Sequences 2008, 2, pp. 187-199, 2008 Bentham Science Publishers Ltd.
Thomsen, et al. "Monitoring endangered freshwater biodiversity using environmental DNA" Molecular Ecology (2012) 21, 2565-2573 (doi: 10.1111/j.1365-294X.2011.05418.x) 2011 Blackwell Publishing Ltd., 9 pages.
Hajibabaei, et al. "Design and applicability of DNA arrays and DNA barcodes in biodiversity monitoring" BMC Biology, 2007; vol. 5:24 (doi: 10.1186/1741-7007-5-24), 7 pages.
Andersen et al. "Meta-barcoding of 'dirt' DNA from soil reflects vertebrate biodiversity" article in Molecular Ecology (2012), 21(8); 1966-1979 (doi: 10.1111/j.1365-294X.2011.05261.x)2011 Blackwell Publishing Ltd., 15 pages.
Chang et al."a molecular forensic method for identifying species composition of processed marine mammal meats" Journal of Forensic and Legal Medicine, Mar. 23 2014, pp. 65-69.

\* cited by examiner

*Primary Examiner* — David C Thomas
(74) *Attorney, Agent, or Firm* — Bond Schoeneck and King PLLC; David Nocilly; George McGuire

(57) ABSTRACT

A method for characterizing at least a portion of the biodiversity of a sample. The method includes the steps of: (i) obtaining a sample having nucleic acid from a plurality of different organisms; (ii) extracting at least a portion of the nucleic acid from the sample; (iii) optionally performing a whole-genome amplification of the extracted nucleic acid; (iv) optionally performing a second, targeted amplification; (v) sequencing the amplified nucleic acid to obtain sequence data comprising a nucleic acid sequence for at least some of the plurality of different organisms; (vi) querying, using the obtained sequence data, a sequence database, where querying the sequence database identifies one or more of the plurality of different organisms; and (vii) determining, using the identified one or more of the plurality of different organisms, a characteristic of the sample.

10 Claims, 9 Drawing Sheets

UNIVERSAL DNA PROFILING

CROSS-REFERENCE TO RELATED APPLICATIONS

This application claims priority to U.S. Provisional Patent Application Ser. No. 62/232,007, filed on Sep. 24, 2015 and entitled "Universal DNA Profiling," the entire disclosure of which is incorporated herein by reference.

FIELD OF THE INVENTION

The present disclosure is directed generally to methods and systems for characterizing the breadth of DNA biodiversity present in a sample.

BACKGROUND

It is often important, for example in forensic research and analysis, to be able to determine the origin of a person or object or the path that the person or object has recently traveled. It can also be important for many other applications, for example, to sample and characterize the DNA biodiversity present in or on a person or object, including but not limited to bacteria, fungi, plant, micro- and other invertebrates, domesticated animals, and humans, among many others.

While there have been advances in the use of DNA as a source of investigative intelligence in fields such as forensics, there has not been a concerted effort to leverage the complete interspecific set of DNAs collected from an object or person of interest. For example, a package of concern acquired after being sent through the mail would commonly be analyzed with a primary focus on the identity of the humans who came into physical contact with the package. These analytical foci, especially for human identification purposes, have proven to be useful in investigations and criminal prosecutions; however there are limitations dependent upon the complexity of DNA deposited by a single species.

However, single-species targeting fails to leverage other DNA signatures that can provide additional, highly informative, data. This narrow approach does not take advantage of all possible DNA present, which can be used for identity and geolocation decision-making. The diversity of DNAs expected include those coming from pollen, bacteria, fungi, micro-invertebrates associated with humans, geospatial indicator species, and traces of domestic animals and native wildlife, among many other possibilities. If properly analyzed, the breadth, distributions, and levels of DNAs present from this wide variety of organisms would provide an unprecedented array of biological signatures that can be applied for intelligence applications. Characterization of these DNA signatures followed by association with particular locations or individuals could then be used to corroborate intelligence collected through alternate means, including a single-species analysis, and more traditional research.

Accordingly, there is a continued need in the art for methods and systems of sample analysis that characterize the full breadth of DNA biodiversity present on or in the sample, thereby enabling more precise DNA-based geolocation.

SUMMARY OF THE INVENTION

The present disclosure is directed to inventive methods and systems for characterizing the DNA biodiversity present on or in a sample using next-generation DNA sequencing to obtain DNA sequence data from enriched DNA targets. The method and system provides unprecedented DNA-based geolocation of an object based on analysis of a full DNA profile for the DNA biodiversity deposited on a surface, compared to previously single-species methods.

According to an embodiment, the methods described or otherwise envisioned herein refer to a novel method for identifying or typing all known sources of eukaryotic cells within a sample. The method is in contrast to the prior art practice of metagenomic analysis, which focuses on the total prokaryotic contribution to an environmental sample. Accordingly, the methods described or otherwise envisioned herein include one or more steps to enrich a sample for eukaryotic DNAs, thus removing prokaryotic contaminates from the sample. This enrichment (i.e. filtering) leads to an increasingly optimal sequencing run and, as a result, simplified and more informative conclusions regarding the eukaryotic diversity within the sample.

According to an embodiment, a sample is obtained and total DNA extraction is performed to ensure collection of all DNAs present on or in the sample. The DNA is then subjected to whole-genome amplification. A second enriching process is then performed, which will preferentially target the most informative phylogenetic (e.g., identity) markers. This approach uses sequence-specific purification methods that enable an increased ability to obtain discriminatory and thus highly informative DNAs relative to the rest of the DNA sequences present. For example, the enrichment techniques can use conserved and specific biotinylated capture probes with sequence similarity/identity to conserved genes identified above. DNAs with sequences complimentary to the capture probes will hybridize and subsequently be purified using Streptavidin-bound magnetic beads. Next, next-generation DNA sequencing is used to obtain DNA sequence data from the enriched DNA targets. The obtained DNA sequences will then be deconvoluted and classified by multiple query approaches against locally-stored and/or public databases, such as the GenBank non-redundant (NR) database. According to an embodiment, this can be assessed locally using NCBI-BLAST and internally developed analytical techniques and software suites. According to one embodiment, DNA sequences that are completely absent from the databases or that have suboptimal identity scores can be sequentially evaluated using alignment and nonalignment-based DNA sequence clustering to arrive likely genus/species closest matches.

The conserved regions of DNA provide a key to accessing information from a sample of interest. Their conservation maintains functionality, but the sequence uniformity is not absolute. That is, sequence diversity exists among taxonomic levels—and individuals within them—that permits their exploitation as diagnostic markers. According to an embodiment, the universal DNA profile assessment methods and systems enable high-confidence conclusions about sample geolocation, origin, travel routes, transport methods/conditions, handlers and associated interactions.

According to an aspect is a method for characterizing biodiversity of a sample. The method includes the steps of: (i) obtaining a sample comprising nucleic acid from a plurality of different organisms; (ii) extracting at least a portion of the nucleic acid from the sample; (iii) performing an amplification of the extracted nucleic acid; (iv) sequencing the amplified nucleic acid to obtain sequence data comprising a nucleic acid sequence for at least some of the plurality of different organisms; (v) querying, using the obtained sequence data, a sequence database, wherein querying the sequence database identifies one or more of the plurality of different organisms in the sample; and (vi) determining, using the identified one or more of the plurality of different organisms, a characteristic of the sample.

According to an embodiment, the amplification step comprises whole-genome amplification.

According to an embodiment, the amplification step comprises targeted amplification.

According to an embodiment, the targeted amplification comprises amplification of at least one DNA sequence, wherein the DNA sequence is conserved among a plurality of organisms.

According to an embodiment, the method further includes a second amplification, wherein the second amplification step comprises targeted amplification.

According to an embodiment, the querying step comprises comparing the obtained sequence data to a plurality of sequences within the sequence database, and further comprises identifying, for each of the sequences within the obtained sequence data, a sequence within the sequence database that most closely matches the respective one of each of the sequences within the obtained sequence data.

According to an embodiment, the determining step comprises a determination of the geographic distribution of the identified organisms in the sample.

According to an embodiment, the determined characteristic is a probable location of the sample. According to an embodiment, the determined characteristic is a source of the sample.

According to an embodiment, the method further includes the step of generating a report of the identified organisms in the sample.

According to an embodiment, the report comprises a summary of the identified organisms in the sample. According to an embodiment, the report comprises a representation of the geographic distribution of the identified organisms in the sample. According to an embodiment, the report comprises a map.

According to another aspect is a method for characterizing at least a portion of the biodiversity of a sample. The method includes the steps of: (i) obtaining a sample comprising nucleic acid from a plurality of different organisms; (ii) extracting at least a portion of the nucleic acid from the sample; (iii) performing a first amplification of the extracted nucleic acid, wherein the first amplification comprises whole-genome amplification; (iv) performing a second amplification using the product of the first amplification, wherein the second amplification comprises a targeted amplification; (v) sequencing the amplified nucleic acid to obtain sequence data comprising a nucleic acid sequence for at least some of the plurality of different organisms; (vi) querying, using the obtained sequence data, a sequence database, wherein querying the sequence database identifies one or more of the plurality of different organisms in the sample; and (vii) generating a report of the identified organisms in the sample.

According to yet another aspect is a method for characterizing the biodiversity of a sample. The method includes the steps of: (i) obtaining a sample comprising nucleic acid from a plurality of different organisms; (ii) extracting at least a portion of the nucleic acid from the sample; (iii) performing a first amplification of the extracted nucleic acid, wherein the first amplification comprises whole-genome amplification; (iv) performing a second amplification using the product of the first amplification, wherein the second amplification comprises a targeted amplification; (v) sequencing the amplified nucleic acid to obtain sequence data comprising a nucleic acid sequence for at least some of the plurality of different organisms; (vi) querying, using the obtained sequence data, a sequence database, wherein querying the sequence database identifies one or more of the plurality of different organisms in the sample; (vii) determining, using the identified one or more of the plurality of different organisms, a characteristic of the sample, wherein the characteristic is a geographic distribution of the identified organisms in the sample; and (viii) generating a report of the identified organisms in the sample, wherein the report comprises a representation of the geographic distribution of the identified organisms in the sample.

These and other aspects of the invention will become clear in the detailed description set forth below.

BRIEF DESCRIPTION OF THE DRAWINGS

The present invention will be more fully understood and appreciated by reading the following Detailed Description in conjunction with the accompanying drawings.

DETAILED DESCRIPTION

Figure 1:
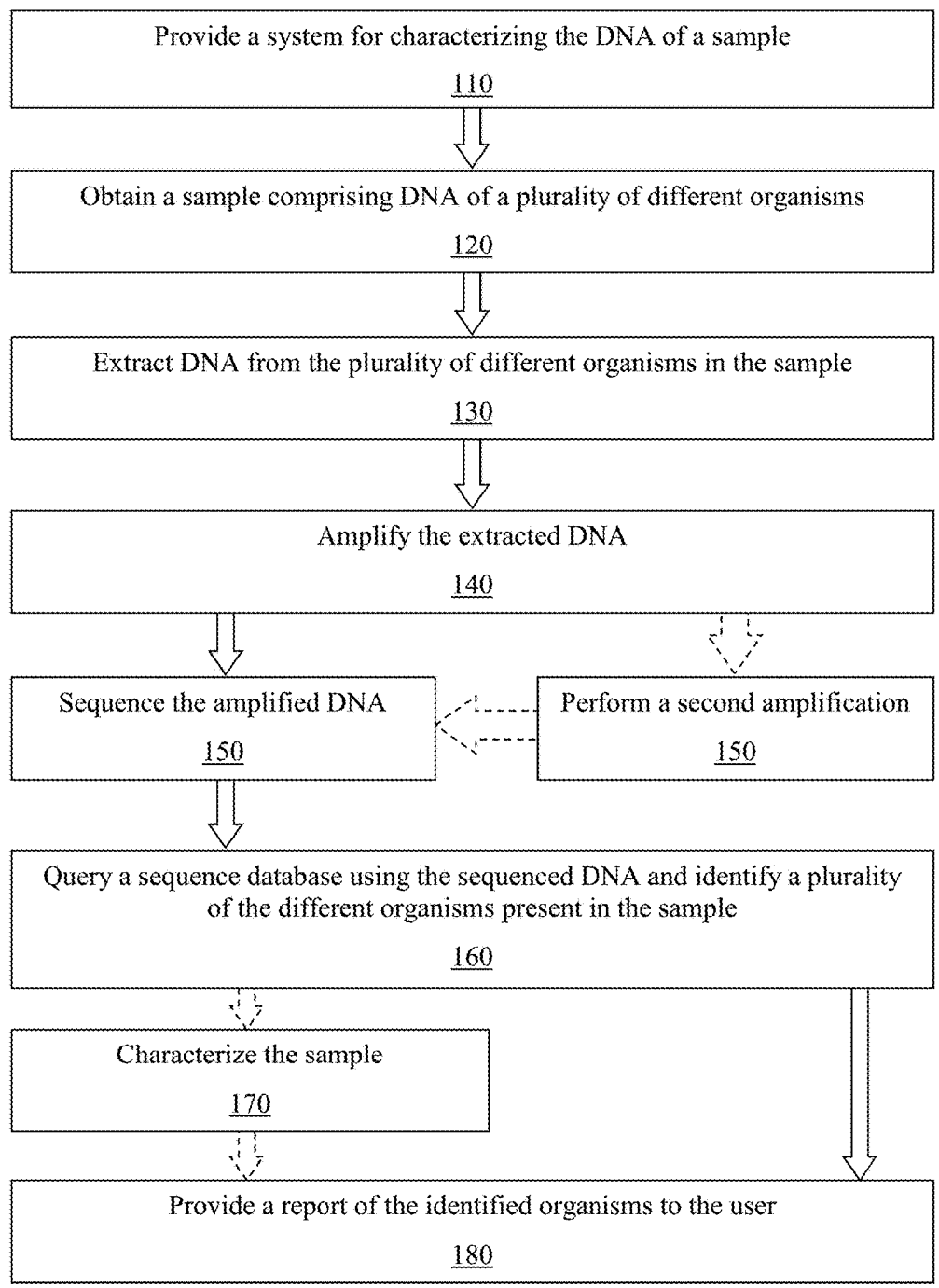
FIG. 1 is a flowchart of a method for characterizing at least a portion of the biodiversity of a sample using DNA, in accordance with an embodiment.

The present disclosure provides methods and systems for characterizing the DNA biodiversity present on or in the sample by amplifying targeted phylogenetic markers and using next-generation DNA sequencing to obtain DNA sequence data from the enriched DNA targets. The sequence data is then analyzed by comparing to databases of phylogenetic markers in order to identify the organisms that were present in or on the sample. The obtained biodiversity can then be utilized for downstream analysis such as sample geolocation, origin, travel routes, transport methods/conditions, handlers and associated interactions.

According to an embodiment, the methods and systems described or otherwise envisioned herein are utilized to characterize the breadth of DNA biodiversity present in a sample, including but not limited to bacteria, fungi, plants, micro- and other invertebrates, domesticated animals, and humans. The method and system includes the identification of a panel of conserved genes that can serve as universal DNA-based markers and are utilized to target a maximum number of known and already cataloged species. These genes consist of characterized organismal phylogenetic markers such as ribosomal DNA, mitochondrial sequences, and the F-Box gene family, among many other possible regions, genes, or sequences. It is anticipated that a selection of these genes may be capable of achieving resolution to the sub-species, population, or individual levels.

According to an embodiment, total DNA extraction will be performed to ensure collection of all DNAs that may be present in or on a sample for analysis. Following DNA extraction is a DNA enrichment step. According to an embodiment, the DNA is subjected to standard whole genome amplification (WGA). This can offer the advantage that any DNAs present at low levels can be faithfully amplified to substantial concentration levels that allow for detection and analysis and for repeated assessments.

While WGA produces a higher abundance of the DNAs present on a sample, the need for targeting certain regions in the DNAs to target the most informative phylogenetic (e.g., identity) markers can be recognized. Thus, a second enriching process that will preferentially retain DNAs for these informative sequences can be optionally be performed. The approach uses sequence-specific purification methods that enable an increased ability to obtain discriminatory and thus highly informative DNAs relative to the rest of the DNA sequences present. The enrichment technique uses conserved and specific biotinylated capture probes with sequence similarity/identity to conserved genes identified above. DNAs with sequences complimentary to the capture probes hybridize and are subsequently purified using Streptavidin-bound magnetic beads.

According to an embodiment, at the next step, conserved gene DNA sequence data is obtained. For example, next-generation DNA sequencing can be used to obtain DNA sequence data from the enriched DNA targets.

According to an embodiment, at the next step, the obtained DNA sequence data can be analyzed. As described herein, the DNA samples acquired from an object of concern are expected to be comprised of a wide variety of DNAs from a diverse set of organisms. Deconvolution and classification of these mixtures of DNA sequences is assessed by one or more queries against locally stored and public databases, such as for example, the GenBank non-redundant (NR) database. This is assessed locally using NCBI-BLAST and internally developed analytical techniques and software suites.

According to an embodiment, DNA sequences that are completely absent from GenBank or that have suboptimal identity scores can be sequentially evaluated using alignment and nonalignment-based DNA sequence clustering to arrive likely genus/species closest matches. Genomic data, including the target DNA sequences can then be initially evaluated using currently available databases. Unique DNA sequences obtained from the internally generated samples.

Referring to FIG. 1, in one embodiment, is a method 100 for characterizing at least a portion of the biodiversity of a sample using DNA. At step 110, a system for characterizing at least a portion of the biodiversity of a sample using DNA is provided. The system may comprise, for example, a DNA extraction component, a DNA amplification component, a DNA sequencing component, and/or a DNA analysis component, as described or otherwise envisioned herein. The system may be one device or multiple devices. The components of the system may be co-located or may be located at one or more different places. For example, the DNA may be obtained, extracted, amplified, and sequenced at one location, and may be analyzed at a second location. Many other embodiments are possible.

At step 120 of the method, a sample is obtained. The sample preferably comprises nucleic acid from a plurality of different organisms. According to an embodiment, the plurality of different organisms comprises closely related organisms, such as different species of an organism. According to another embodiment, the plurality of different organisms comprises distantly related organisms, such as organisms within different classes or kingdoms. According to yet another embodiment, the plurality of different organisms comprises a combination of distantly and closely related organisms.

At step 130 of the method, at least a portion of the DNA is extracted from the plurality of different organisms in the sample. The DNA can be extracted using one or more of a variety of different DNA extraction methods and techniques known in the art. The goal of the DNA extraction is to extract DNA from all or a majority of the plurality of different organisms in the sample, while ensuring that the extracted DNA can be sequenced in whole or in part. The DNA may be extracted, for example, using a kit or other method of extraction.

The extracted DNA is then filtered via targeted enrichment methods including but not limited to magnetic bead based separation and/or column filtration.

At step 140 of the method, at least a portion of the DNA extracted from the plurality of different organisms in the sample is amplified. According to an embodiment, the DNA undergoes whole genome amplification (WGA). As a result, any DNAs present at low levels within the sample extraction can be amplified to higher concentration levels, thereby allowing for improved detection and analysis.

According to another embodiment, the amplification targets one or more target regions within the DNA sequence of one or more of the plurality of different organisms in the sample. For example, the target regions will potentially be, for example, informative phylogenetic markers. Accordingly, at optional step 142 of the method, a second amplification is performed to amplify one or more target regions within the DNA sequence of one or more of the plurality of different organisms in the sample. The second amplification step will preferentially retain DNAs for informative sequences. The approach uses sequence-specific purification methods that enable an increased ability to obtain discriminatory and thus highly informative DNAs relative to the rest of the DNA sequences present.

According to an embodiment, one or more conserved genes, regions, or DNA sequences are identified which can serve as universal DNA-based markers and can be utilized to target a maximum number of known and already cataloged species. For example, the genes, regions, or DNA sequences may comprise one or more known or identified organismal phylogenetic markers such as ribosomal DNA, mitochondrial sequences, and/or genes of the F-Box family, among many other possible regions, genes, or sequences. According to an embodiment, a selection of these genes is capable of achieving resolution to the sub-species, population, and/or individual levels.

According to one embodiment, the enrichment technique can utilize conserved and/or specific biotinylated capture probes with sequence similarity/identity to conserved genes. DNAs with sequences complimentary to the capture probes hybridize and are subsequently purified using Streptavidin-bound magnetic beads. Many other methods are possible.

At step 150 of the method, the amplified nucleic acid is sequenced, thereby obtaining sequence data comprising a nucleic acid sequence for at least some of the plurality of different organisms within the sample. The amplified nucleic acid can be sequenced using one or more of a plurality of known methods or systems for sequencing DNA. The sequencing may target known or identified regions, such as the regions targeted for amplification in one or more prior steps, or may be whole-genome sequencing (WGS). Any of a variety of WGS methods or systems may be utilized.

At step 160 of the method, the obtained sequence data is utilized to identify one or more of the plurality of different organisms in the sample. According to an embodiment, a sequence database is queried using the obtained sequence data. The obtained sequence data is compared to the plurality of sequences in the database, and a sequence that is sufficiently similar to a sequence in the database is considered identified and thereby present in the sample.

Since the sample comprises DNA from a plurality of different organisms, deconvolution and classification of the mixture of DNA sequences can be assessed by one or more queries against locally stored and/or public databases, including but not limited to the GenBank non-redundant (NR) database, among many others. The analysis can be assessed locally using NCBI-BLAST and internally developed analytical techniques and software suites. According to an embodiment, a DNA sequence absent from GenBank or having a suboptimal identity score can be sequentially evaluated using alignment and nonalignment-based DNA sequence clustering to arrive at a likely genus/species match or closest match. Genomic data, including the target DNA sequences can then be initially evaluated using currently available databases. Unique DNA sequences obtained from the internally generated samples.

At optional step 170 of the method, according to an embodiment, the sample is characterized using information about the one or more of the plurality of different organisms, a characteristic of the sample. For example, the characterization could be identification or probability of identification of the sample, identification or probability of the location or source of the sample, and/or identification of one or more other current, past, or future characteristics of the sample.

According to one embodiment, for example, the characterization is or can include a determination or estimate or probability of the geographic distribution of the plurality of species identified in the sample. Accordingly, this could comprise querying one or more databases for information about location, range, and/or origin of the identified species. As another example, the characterization is or can include a determination or estimate or probability of the likelihood of characterizing geolocation based on overlap analysis of identified species ranges. For example, probabilities can be assigned to locations based on the obtained sequence and species data. As another example, the characterization is or can include a determination or estimate or probability of developing and using a database and/or interface with a mapping service such as Google Earth, among many other possible mapping services. This provides a user interface that displays information, such as geolocation information, to the user. The user interface could include not only mapping information, but also species identification information, either separately or as an overlay on a map. Many other characterizations are possible.

At step 180 of the method, a report of the identified one or more of the plurality of different organisms, and/or the determined characteristic of the sample, is generated. The report can take many different forms and/or many different types of media, as described or otherwise envisioned herein.

Materials and Methods

Sample Collection

Samples were collected from the sole of the right shoe worn by two individuals in a 24-hour period. This substrate enables the passive collection of DNAs present in the locations in which the wearer traveled. Relative to alternative substrates, there is an expectation that a high level of biodiversity will be encountered in the resulting sequence data due to the constant contact of the sole with a variety of indoor and outdoor surfaces. Additionally, the coupled pressure and friction forces that are present during each step allows for a higher potential of transfer and retention of the DNAs onto the substrate.

The right shoe soles were decontaminated with a 10% bleach solution and subsequently rinsed with reagent grade 70% ethanol and sterile DI-$H_2O$. Pre-exposure control samples were collected from the sole of the right shoe immediately following decontamination. Two sterile swabs moistened with sterile DI-$H_2O$ were simultaneously used to sample the entire sole of the right shoe. The shoes were then worn continuously throughout the remainder of the evening and again the following day. At the conclusion of the work day the individual samples the sole of the right shoe, using two swabs as previously described.

The experimental swabs from the sole were extracted using a hybrid plant/animal tissue Qiagen kit-based protocol. Control swabs were not extracted at this time. Subsequently, 10 ng of DNA extract was subjected to whole genome amplification using the Genomiphi v2 whole genome amplification kit (GE Life Sciences). The samples were then subjected to next generation 454 shotgun DNA sequencing in order to obtain sequence data for analysis and organism identification.

Figure 2:
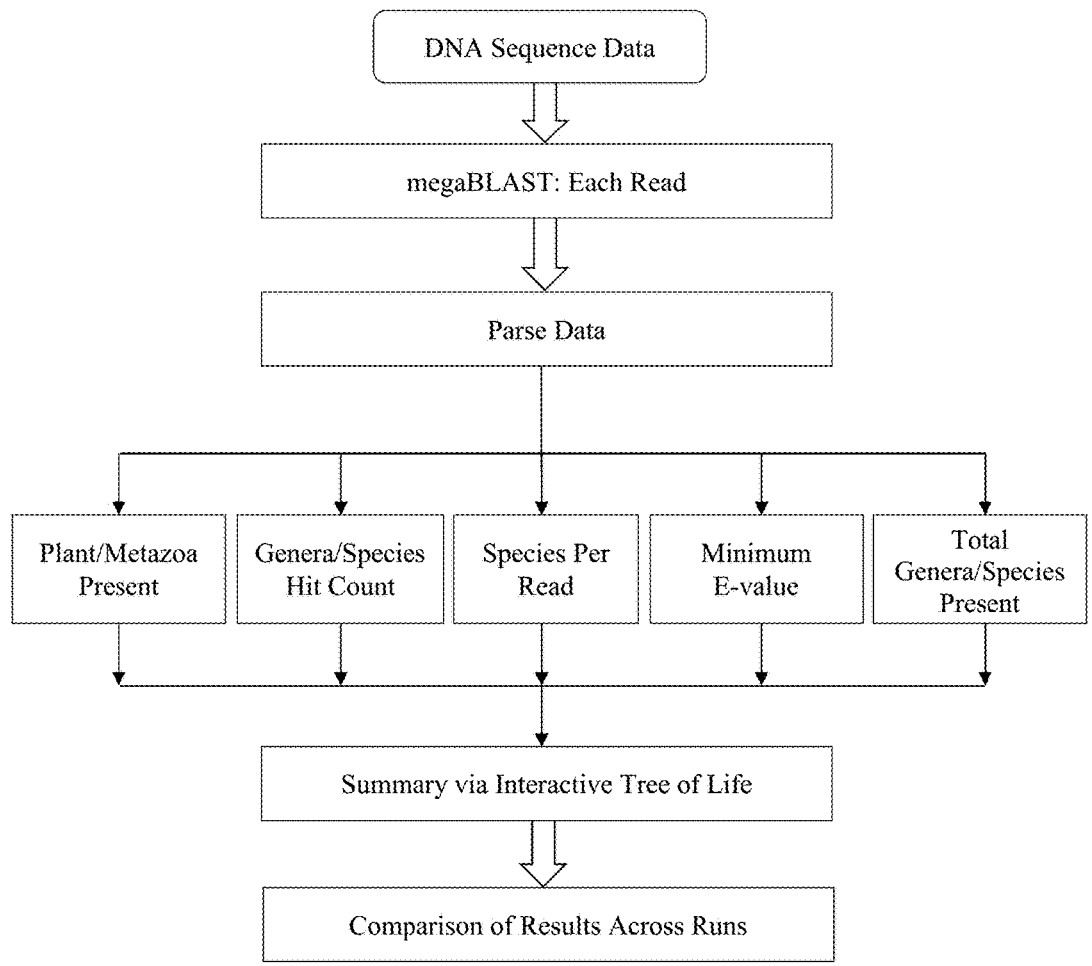
FIG. 2 is a data analysis schema for universal DNA profiling, in accordance with an embodiment.

Shown in FIG. 2, for example, is a possible data analysis schema for universal DNA profiling. According to an embodiment, the expectation of obtaining between 30 and 50 million bases of DNA sequence data requires one or more bioinformatics approaches to parse the data. For example, sequence reads can be subjected to a batch megaBLAST. This allows for an initial filtering of data by exclusively returning nucleotide sequences having high sequence identity. Data parsing can then proceed using a variety of Python and Perl scripts. These scripts will parse the data based on the genera and species present, minimum E-values(high confidence hits), the species present per read, the number of hits per genus and species and the summary of hits from the Plant and Animal (Metazoan) kingdoms. The Interactive Tree of Life (iTOL) will be used to summarize intra-run data. Inter-run data will be compared based on unique species observed.

Results—Experiment #1

Post whole genome amplification DNA quantities of over 1 μg were obtained. Sequencing library preparation used approximately 750 ng of the WGA sample. All quality control benchmarks were surpassed in the subsequent 454 shotgun sequencing run, as shown in TABLE 1.

TABLE 1

| GS Jr Shotgun Sequencing Run | |
| --- | --- |
| Average read length | 437 bases |
| Total bases | 58 million |
| Total reads | 133,000 |

In the absence of laboratory methods which allow for filtering of sequence, the parsing of sequence data remained laborious and critical to this study. The sequence data was subjected to a megaBLAST using a locally running NCBI BLAST database residing on a high performance computer (250 GB RAM). With only high confidence (low evalue, high identity) results returned by megaBLAST post-hoc data analysis consisted of analysis of the raw data returned by megaBLAST by first using an initial data filter to parse based on E-values<$1 \times 10^{-4}$. Further data parsing was performed to return those data that exhibited to lowest E-value, indicating the strongest hits per read.

Figure 3:
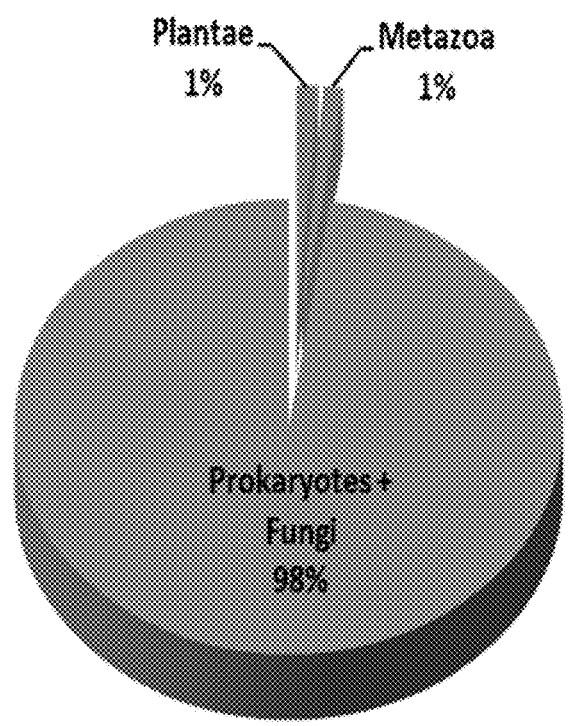
FIG. 3 is a graph of a representative megaBLAST hit summary based on domain/kingdom, in accordance with an embodiment.

The megaBLAST returned 63,041 reads that had significant hits, of these plantae and metazoan hits were less than 2.5% of the total hits, with counts 811 and 729 respectively, as shown in FIG. 3. The initial parsed data displayed 3,702 unique genera consisting of 8,716 unique species. Upon selection of those hits which had the lowest E-value per read, 966 unique species were obtained. Of these 966 species 86.6% consisted of prokaryotes or fungi, although potentially informative, the resources for biodiversity and geographical distributions do not compare to the breadth of that of the plant and metazoan kingdoms. In addition, prokaryotes have higher mutation rates which may complicate their use as a key indicator for geolocation.

Figure 4:
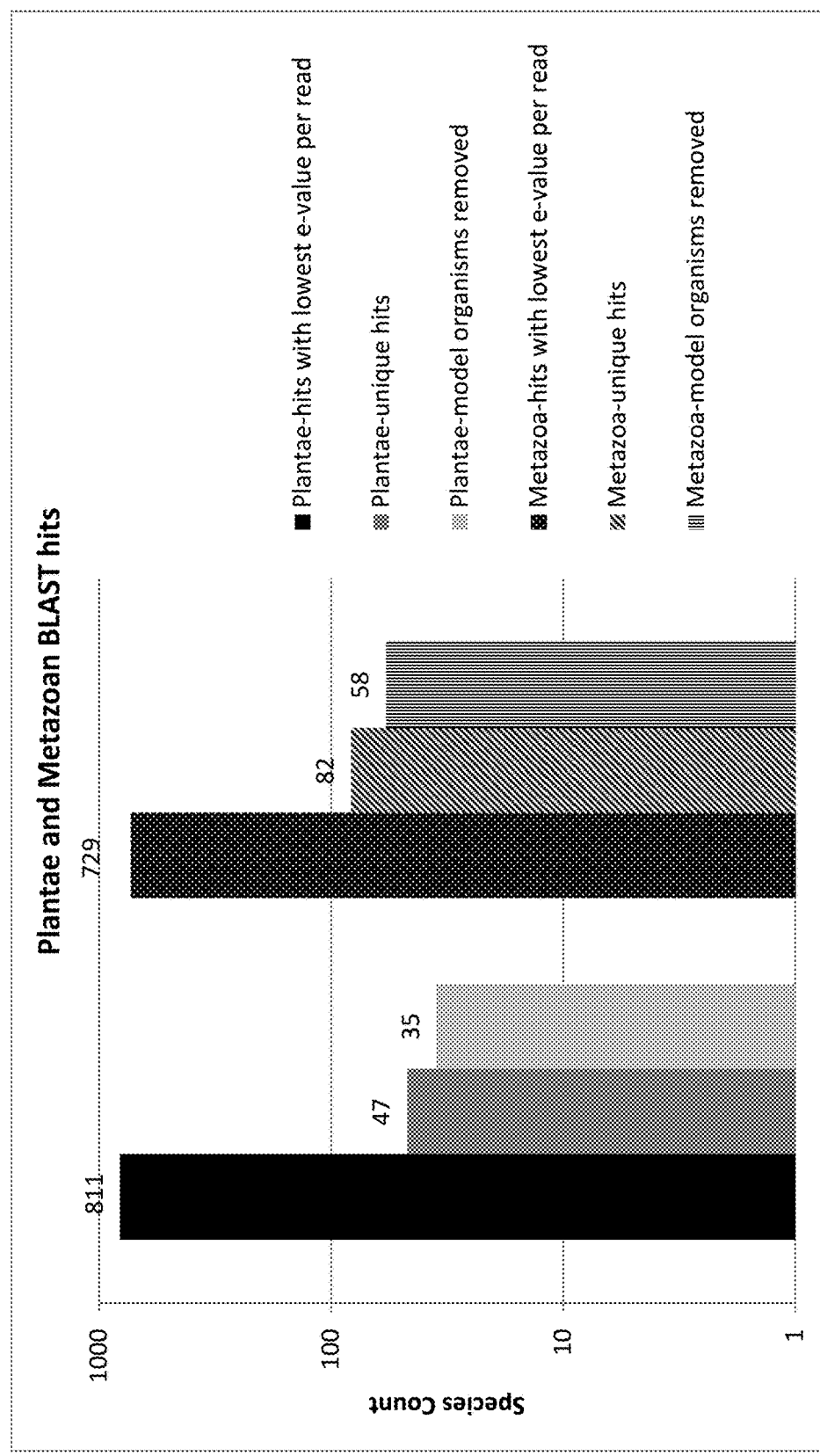
FIG. 4 is a graph of a representative megaBLAST hit summary for organisms in the Plantae and Metazoan kingdoms, in accordance with an embodiment.
Figure 5:
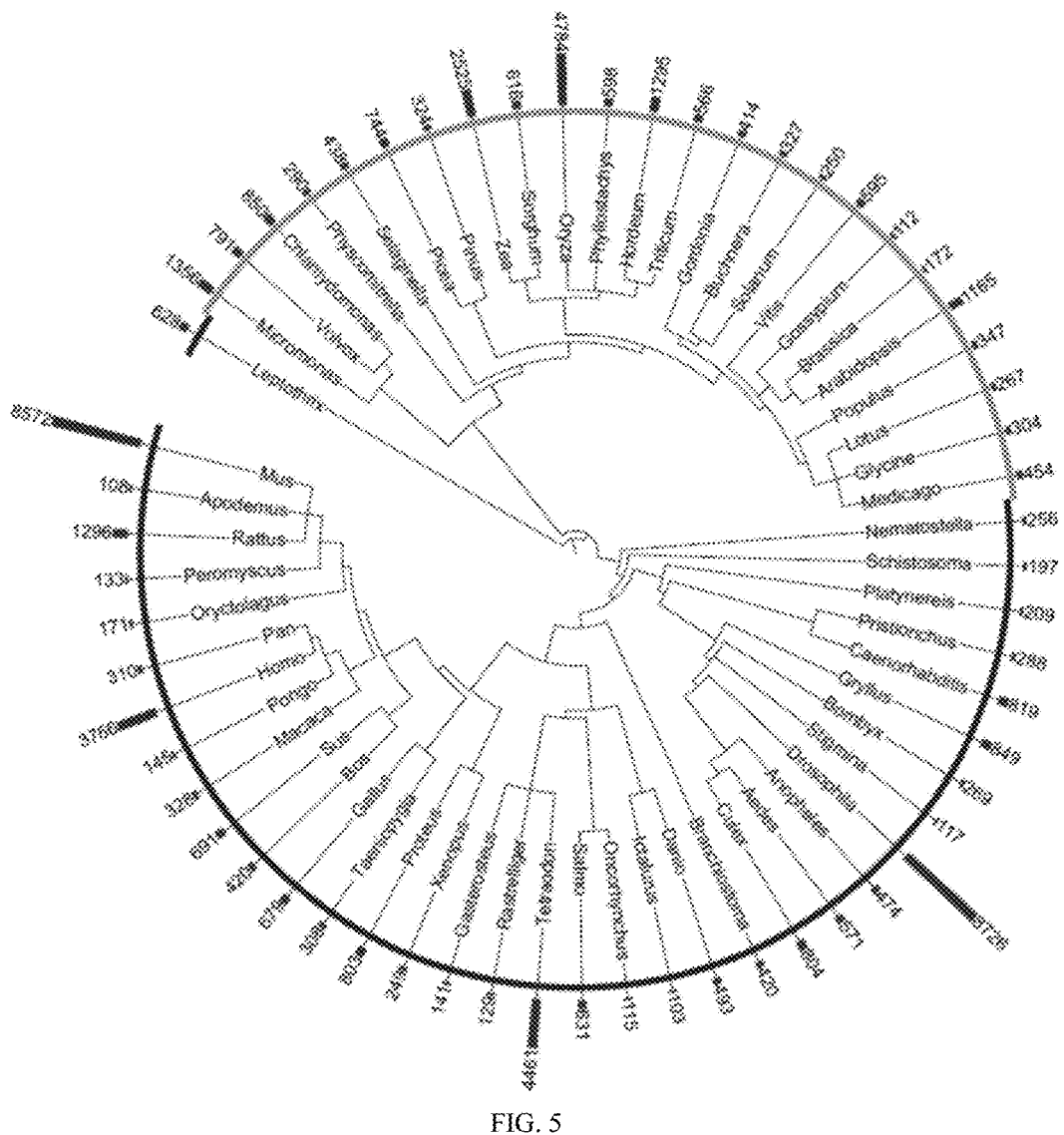
FIG. 5 is a graph of genera from the Plantae and Metazoan kingdoms with a minimum of 100 hits obtained from BLAST of shotgun sequence data, in accordance with an embodiment.

With a primary focus on those hits which returned significant hits to organisms in the Plantae and Metazoan kingdoms, once unique hits and model organisms were removed only 35 hits to plants and 58 to animals remained, as shown in FIG. 4. In addition, to better visualize the returned plant and animal hits, the genera which had 100+ hits were uploaded to the interactive tree of life, as shown in FIG. 5.

According to an embodiment, the system and methods can also be utilized to target eukaryotes, specifically those from the plant and animal kingdoms, as organisms from these taxonomic groups will likely yield the most informative data.

Results—Experiment #1

According to an embodiment, an additional series of experiments were performed using additional samples. For example, for a sample labeled "MCD," DNA was obtained from a shoe bottom that had been worn in several places around Geneva and Syracuse, N.Y. A second sample labeled "MM" was collected from a shoe having been worn in and around the east side of Syracuse, N.Y.

TABLE 2

Summary Statistics for Sample MCD

| MCD # unique genera | MCD # unique species | MCD # unique plant and animal species | # species common between MCD and MM (plants & animals) | # species specific to MCD (plants & animals) |
|---|---|---|---|---|
| 505 | 943 | 72 | 477 (57) | 450 (26) |

Figure 6:
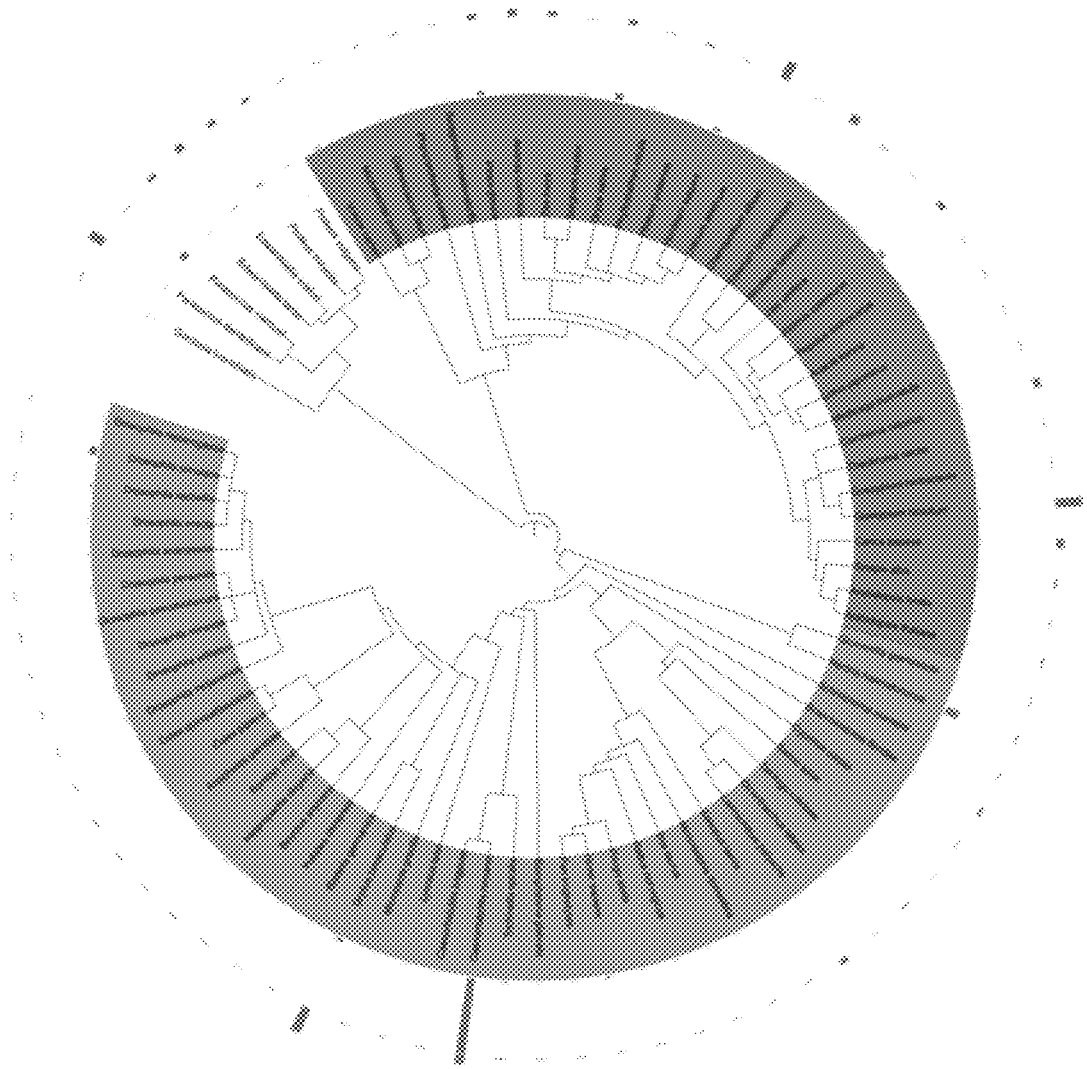
FIG. 6 is an Interactive Tree of Life (iTOL) representation of plant and animal species identified in MCD sample, in accordance with an embodiment.
Figure 7:
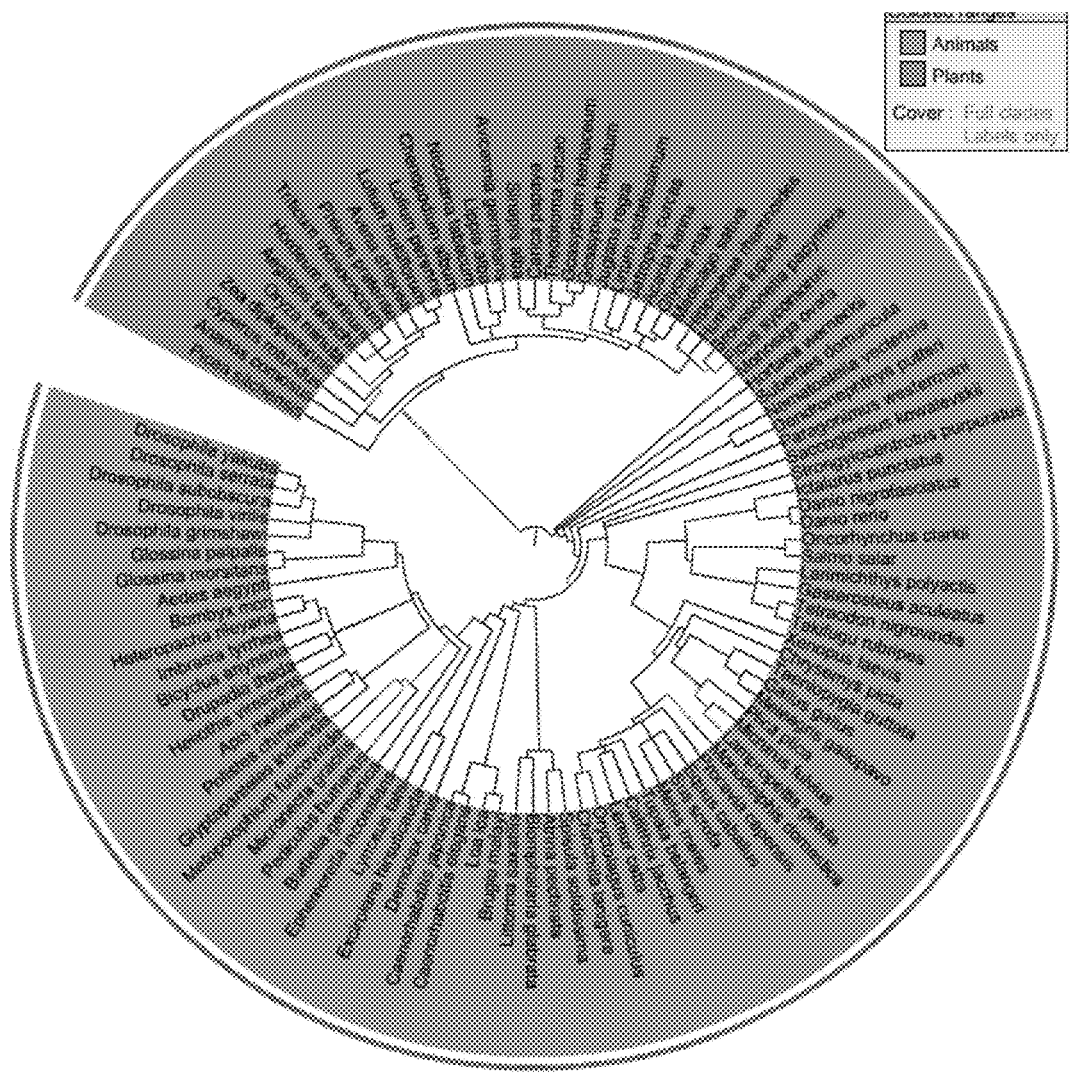
FIG. 7 is an iTOL representation of species unique to either an MCD or MM sample, in accordance with an embodiment.

TABLE 2 provides the summary statistics for the 454 sequence data generated for sample MCD. The vast majority of sequences showed significant similarity to bacteria and fungi which are omnipresent in the global environment and will do little to inform geolocation. In contrast, plants and animals are far more likely to have definable ranges, thus FIG. 6 shows plants (top half) and animals (bottom half) with only a small subset of microbes (not shaded). Bars indicate the number of times that species is found in a dataset and indicate the most significant e-value associated with that species. Therefore, a species with a large bar was found many times with high confidence in the dataset. A number of species identified were found to be unique to either the MCD or MM sample (see TABLE 2) and are represented in FIG. 7.

Figure 8A:
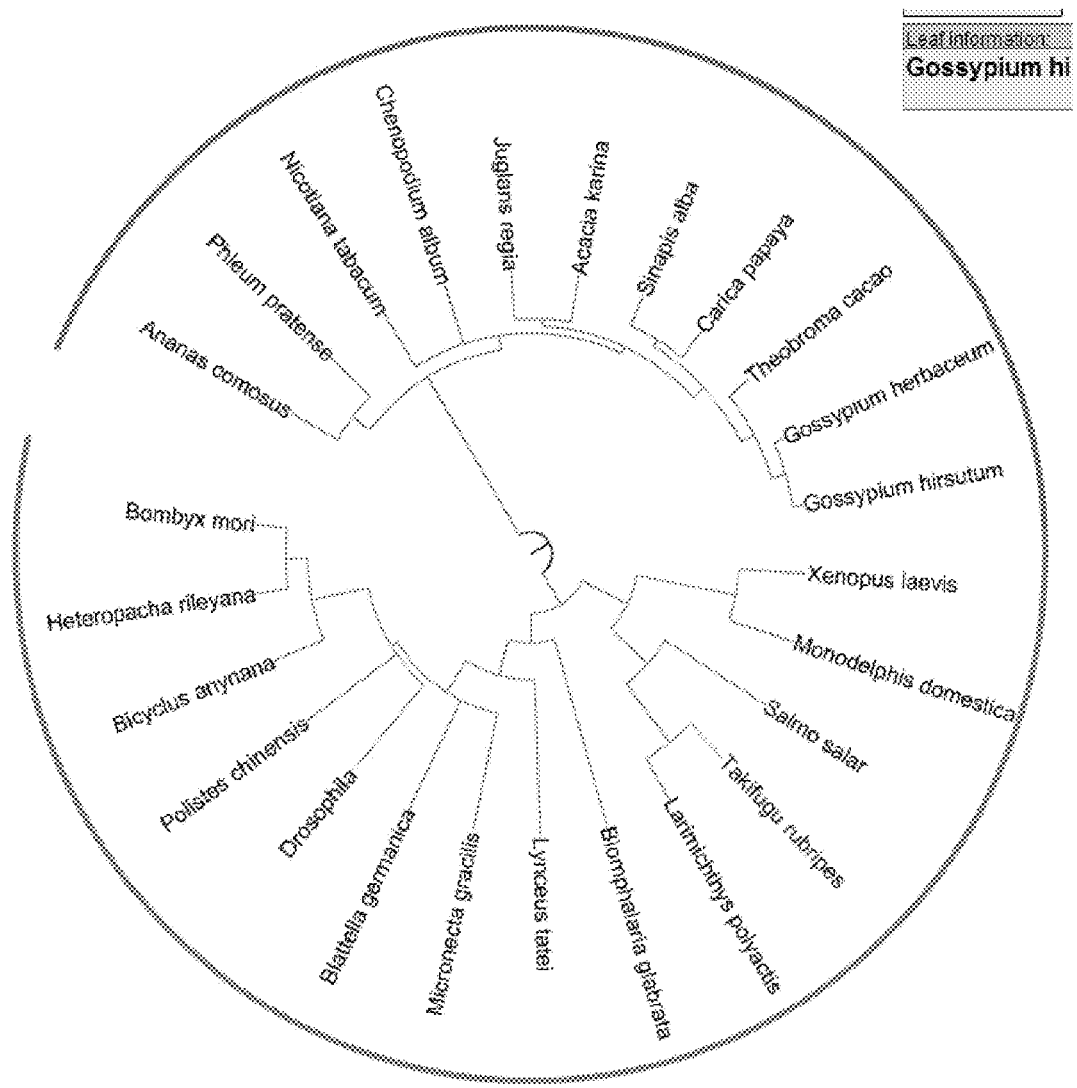
FIG. 8A is an iTOL representation of sequences unique to an MCD sample, in which the MCD has 26 unique species (42% plants; 58% animals), in accordance with an embodiment.
Figure 8B:
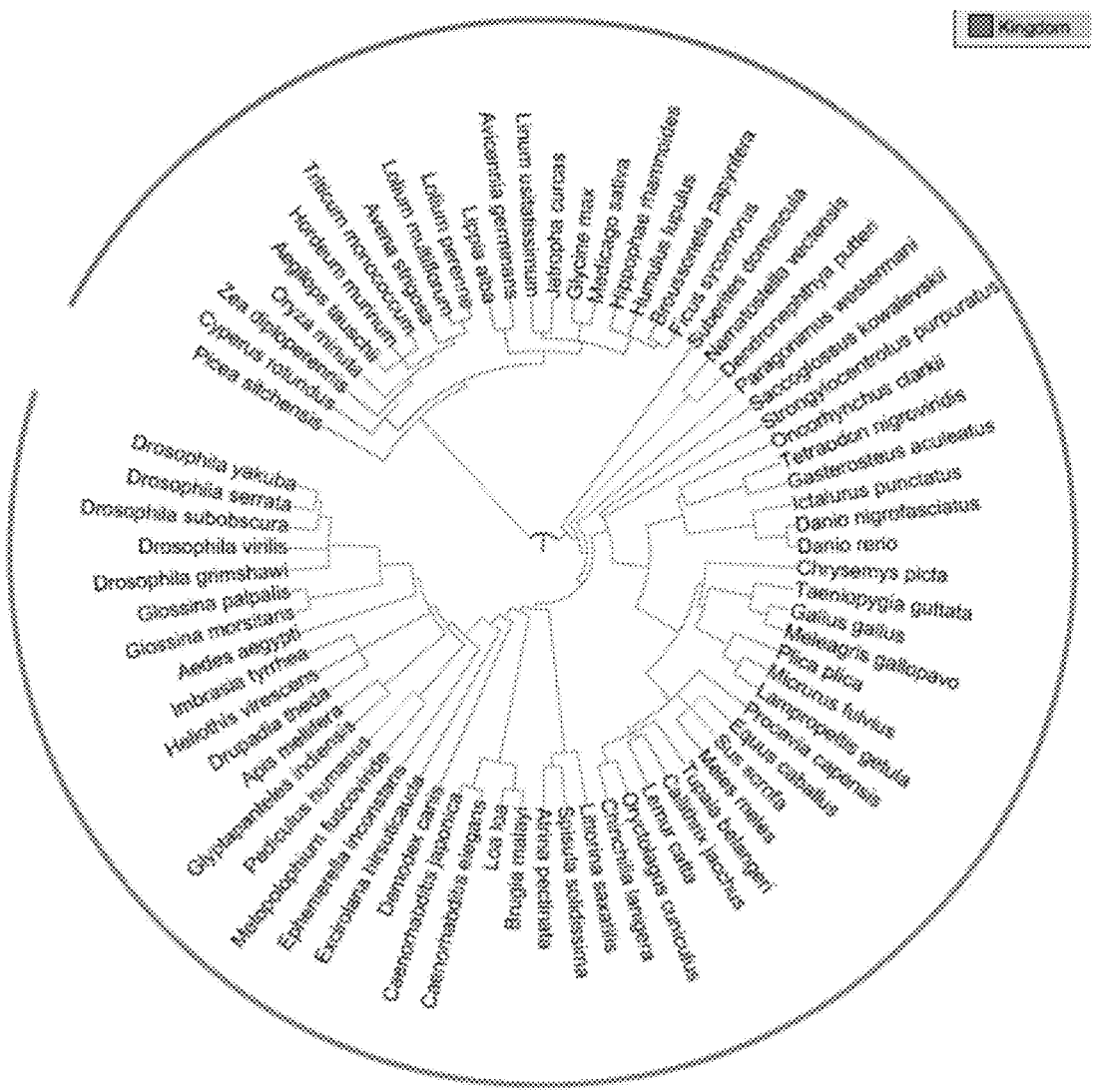
FIG. 8B is an iTOL representation of sequences unique to an MM sample, in which the MM has 78 unique (29.5% plants; 70.5% animals), in accordance with an embodiment.

Shown in FIG. 8A, for example, is an iTOL representation of sequences unique to the MCD sample, in which the MCD has 26 unique species (42% plants; 58% animals). Similarly, shown in FIG. 8B is an iTOL representation of sequences unique to the MM sample, in which the MM has 78 unique (29.5% plants; 70.5% animals).

Where bacterial and fungal sequences may be useful for many different applications, one current goal of geolocation can be further met by analyzing species with well-defined and characterized ranges, such as plants and animals. Accordingly, the methods and systems described or otherwise envisioned herein can include technical selection in the laboratory that will filter out microbial sequences and/or focus specifically on organism with well-defined and well-characterized localization and/or ranges. Additionally, specific sequences can be targeted and sequenced deeply rather than the analysis of all sequences in the sample regardless of their ability to geolocate.

Another embodiment comprises region and/or sequence-specific extraction. For example, biotinylated DNA probes and a bead pull-down method can be utilized to hybridize to and extract informative DNA sequences prior to PCR amplification. This step could be employed, for example when more information is known about the target sequences and could potentially bypass or eliminate the amplification step required for the amplicon sequencing described below.

Yet another embodiment comprises amplicon sequencing. Primers are developed specifically for informative genes with sufficient conservation across species such that a small number of primer sets could amplify a large number of species. The Primers4clades web tool, among many others for example, could be used to design these primers. The DNA would be amplified from the sample in question and submitted to next-generation sequencing. One or more methods of analysis, including those described herein, could be utilized to characterize the sequence data and thus the sample's biodiversity.

For filtering and/or targeting of sequences, there are a number of possible approaches and targets, including but not limited to 26S Proteasome/F-box; RNases; transposable elements; 16S/18S/ITS/traditional phylogenetic markers; mitochondrial sequences such as Cytochrome C Oxidase I, Twinkle; rpoB (β-sununit of rRNA polymerase); zinc Finger genes-Z1C1; and/or methyltransferase genese-cytosine C5, DNMT2, and many others.

Yet another embodiment comprises additional downstream analysis of the sequencing and species data. For example, the method can include the step of determining the geographic distribution of species identified, which may involve querying one or more databases for information about location, range, and/or origin. As another example, the method can include the step of determining whether geolocation is possible based on overlap analysis of identified species ranges. For example, probabilities can be assigned to locations based on the obtained sequence and species data. As another example, the method can include the step of developing and using a database and/or interface with a mapping service such as Google Earth, among many other possible mapping services. This provides a user interface that displays information, such as geolocation information, to the user. The user interface could include not only mapping information, but also species identification information, either separately or as an overlay on a map.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

What is claimed is:

1. A method for characterizing the biodiversity of a sample taken from an object, the method comprising the steps of:
   obtaining a sample from the object that contains nucleic acid from a plurality of different unknown organisms;
   extracting at least a portion of the nucleic acid of the plurality of different unknown organisms from the sample;
   filtering the extracted nucleic acid to enrich the nucleic acid of the plurality of different unknown organisms;
   performing an amplification of the extracted nucleic acid that targets phylogenetic markers of cataloged organisms;
   sequencing the amplified nucleic acid to obtain sequence data for the phylogenetic markers of the plurality of different unknown organisms;
   querying a sequence database, with the phylogenetic markers to identify the plurality of different organisms; and
   determining, using the identified plurality of different organisms, at least one geographic location for the object from which the sample was taken.

2. The method of claim 1, wherein the targeted amplification comprises amplification of at least one DNA sequence, wherein the DNA sequence is conserved among a plurality of organisms.

3. The method of claim 1, wherein the querying step comprises comparing the obtained sequence data to a plurality of sequences within the sequence database, and further comprises identifying, for each of the sequences within the obtained sequence data, a sequence within the sequence database that most closely matches the respective one of each of the sequences within the obtained sequence data.

4. The method of claim 1, wherein said determining step comprises a determination of the geographic distribution of the identified organisms in the sample.

5. The method of claim 1, wherein the characteristic is a source of the sample.

6. The method of claim 1, further comprising the step of generating a report of the identified organisms in the sample.

7. The method of claim 6, wherein the report comprises a summary of the identified organisms in the sample.

8. The method of claim 6, wherein the report comprises a representation of the geographic distribution of the identified organisms in the sample.

9. The method of claim 8, wherein the report comprises a map.

10. A method for characterizing at least a portion of the biodiversity of a sample taken from an object, the method comprising the steps of:
    obtaining a sample, from the object that contains nucleic acid from a plurality of different unknown organisms;
    extracting at least a portion of the nucleic acid of the plurality of different unknown organisms from the sample;
    filtering the extracted nucleic acid to enrich the nucleic acid of the plurality of different unknown organisms;
    performing an amplification of the extracted nucleic acid that targets phylogenetic markers of cataloged organisms;
    sequencing the amplified nucleic acid to obtain sequence data for the phylogenetic markers of the plurality of different unknown organisms;
    querying a sequence database with the phylogenetic markers to identify plurality of different organisms; and
    generating a report of the identified organisms in the sample that includes at least one geographic location for the object from which the sample was taken based on a geographic distribution of the identified organisms.

* * * * *